US007898667B2

(12) United States Patent
Yamada et al.

(10) Patent No.: US 7,898,667 B2
(45) Date of Patent: Mar. 1, 2011

(54) OPTICAL ELEMENT AND METHOD FOR PREPARING THE SAME, SENSOR APPARATUS AND SENSING METHOD

(75) Inventors: Tomohiro Yamada, Yokohama (JP); Ryo Kuroda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 701 days.

(21) Appl. No.: 11/961,216

(22) Filed: Dec. 20, 2007

(65) Prior Publication Data

US 2010/0097610 A1   Apr. 22, 2010

(30) Foreign Application Priority Data

Dec. 27, 2006   (JP) .............................. 2006-352406

(51) Int. Cl.
*G01N 21/00*   (2006.01)
(52) U.S. Cl. ..................................................... 356/445
(58) Field of Classification Search .......... 356/445–448
See application file for complete search history.

(56) References Cited

U.S. PATENT DOCUMENTS

2005/0045977 A1   3/2005   Lin et al. ..................... 257/428

FOREIGN PATENT DOCUMENTS

| JP | 10-267841 | 10/1998 |
| JP | 2000-356587 | 12/2000 |
| WO | WO 2004/068141 A1 | 8/2004 |

OTHER PUBLICATIONS

U.S. Appl. No. 12/045,335, filed Mar. 10, 2008, Tomohiro Yamada et al., pending.
Amanda J. Haes and Richard P. Van Duyne, et al., "A Localized Surface Plasmon Resonance Biosensor: First Steps Toward an Assay for Alzheimer's Disease", Nano Letters, vol. 4, No. 6, May 4, 2004, pp. 1029-1034.

*Primary Examiner*—Michael P Stafira
(74) *Attorney, Agent, or Firm*—Fitzpatrick, Cella, Harper & Scinto

(57) ABSTRACT

In the fields of biosensing and the like, achievement of high sensitivity and high performance has been demanded in the concentration detection of target substances. In order to meet such demand, disclosed is an optical element utilizing the localized surface plasmon resonance, including: a dielectric substrate; a first group of metal microstructures in which a plurality of metal microstructures is supported on a dielectric substrate in an in-plane direction of the substrate; and a second group of metal microstructures in which a plurality of metal microstructures is disposed in the in-plane direction, and each of the metal microstructures is partially exposed to the outside; wherein the first group of metal microstructures and the second group of metal microstructures are laminated so as to be separated from each other by 100 nm or more.

20 Claims, 14 Drawing Sheets

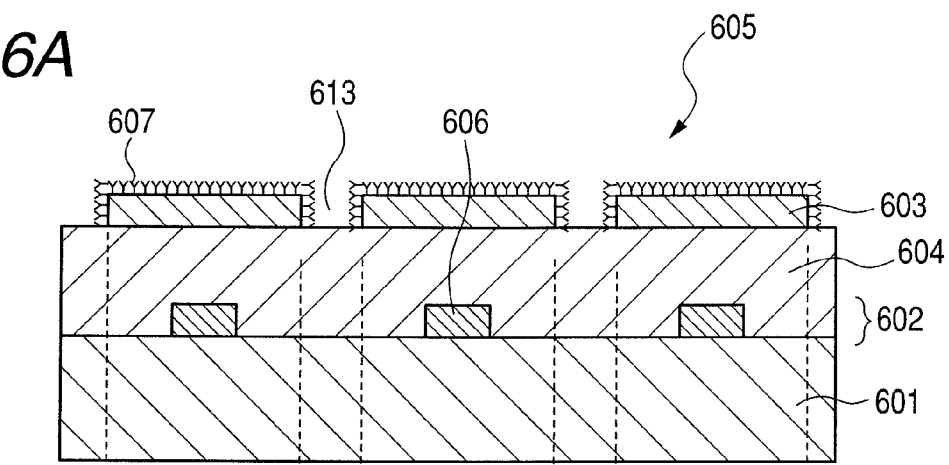
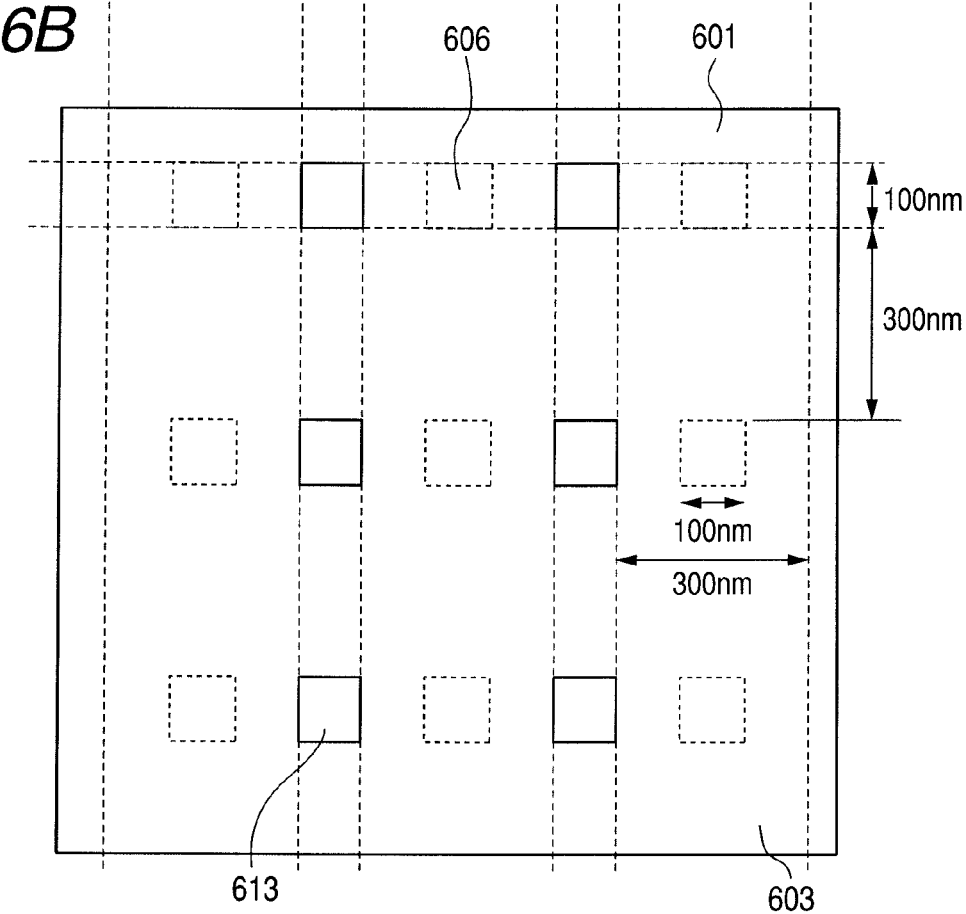

OPTICAL ELEMENT AND METHOD FOR PREPARING THE SAME, SENSOR APPARATUS AND SENSING METHOD

BACKGROUND OF THE INVENTION

1. Field of the Invention

The present invention relates to an optical element having desired optical properties, a sensor apparatus using the optical element, and a sensing method, in particular, to detection of the concentrations of biological molecules.

2. Description of the Related Art

It has been known that localized surface plasmon resonance (hereinafter abbreviated as LSPR) is induced on a minute metal structure. The resonance conditions of LSPR are determined by the refractive index and dielectric constant of the environment surrounding the metal structure. Accordingly, the change of the dielectric constant of the environment surrounding the metal structure can be detected by measuring the change of the optical spectrum of the metal structure by irradiating the metal structure with light to transmit the metal structure.

LSPR is sensitive to the changes of the refractive index and dielectric constant of the environment surrounding the metal structure. Accordingly, LSPR can be applied to a high-sensitivity refractive index sensor. Additionally, as shown below, when the change of the dielectric constant is caused by a biological reaction, application of this phenomenon to a biosensor enables a high-sensitivity sensing, and such a sensing is expected to be widely applied to medical fields and fields of food and environment.

For example, an antigen-antibody reaction can be detected by causing the antigen-antibody reaction to occur in the environment surrounding a metal structure, and by detecting the thereby caused change of the dielectric constant of the environment.

An article by Richard P. Van Duyne et al. in NANO LETTERS, Vol. 4, No. 6, pp. 1029-1034 (2004) discloses an example utilizing as metal structures minute Ag thin-film microparticle structures formed on a flat and smooth substrate, and the antigen concentration has been measured from the change between the optical spectrum for a state where the antibody is attached to the environment surrounding the structures and the optical spectrum for a state where the antigen is further bonded to the antibody. Additionally, the same principle as described above enables to detect a complex formation between an enzyme and a substrate, and a complementary base pair formation based on hybridization of DNA.

Additionally, Japanese Patent Application Laid-Open No. 2000-356587 discloses an example in which Au microparticles are immobilized on a glass substrate, from the spectrum of the plasmon resonance of the Au microparticles, the refractive index of the environment surrounding the microparticles has been detected.

In common transmission measurements including such conventional techniques as described above, the change of the dielectric constant of the environment surrounding the metal particles caused by an antigen-antibody reaction is detected. FIGS. 3A and 3B illustrate a process for such a detection. Specifically, the detection is conducted by measuring the transmission spectra of the metal particles before and after the antigen-antibody reaction, namely, the LSPR optical spectrum (before reaction) 301 and the LSPR optical spectrum (after reaction) 302. The concentration of the antigen is detected from the change of the resonance conditions of LSPR between before and after the reaction (FIG. 3A).

As illustrated in FIG. 3B, the measurement system for the above-described case is schematically as follows: the surface of metal particles 303 is modified with an antibody 305; the metal particles 303 are supported on a dielectric substrate 304 to form a measurement element 306; and the measurement element 306 is irradiated with irradiation light 307 and the transmitted light 308 is detected to measure the transmission spectrum of the measurement element 306.

SUMMARY OF THE INVENTION

When as described above the change of the dielectric constant of the environment surrounding a metal structure is detected as the change of the optical spectral signal based on LSPR, the shape of the measured optical spectrum significantly affects the sensing sensitivity of the detection. Here, conventional techniques have measured the optical spectral signal by detecting as the signal the change of the resonance peak position of LSPR as illustrated in FIGS. 3A and 3B.

However, in general, the resonance peak width of LSPR is broad, and hence the sensing method to detect the peak position shift magnitude as in conventional techniques has involved a problem that the sensing sensitivity improvement is difficult. Accordingly, a new technique for high-sensitivity sensing using LSPR has been demanded.

Thus, in view of the above-described problems, an object of the present invention is to implement a high-sensitivity sensing.

The present invention is directed to an optical element utilizing localized surface plasmon resonance, comprising: a dielectric substrate; a first group of metal microstructures in which a plurality of metal microstructures is supported on the dielectric substrate in an in-plane direction of the substrate; and a second group of metal microstructures in which a plurality of metal microstructures is disposed in the in-plane direction, and each of the metal microstructures is partially exposed to the outside; wherein the first group of metal microstructures and the second group of metal microstructures are laminated so as to be separated from each other by 100 nm or more.

The metal microstructures each can comprise at least one element selected from the group consisting of gold, silver, platinum, copper and aluminum.

The metal microstructures comprised in the first group of metal microstructures or the second group of metal microstructures can be disposed periodically with a specific period A.

The period A can be a length of a natural number times the wavelength of the light that induces surface plasmon on the metal microstructures.

The optical element can comprise a dielectric between the first group of metal microstructures and the second group of metal microstructures.

The distance between the first group of metal microstructures and the second group of metal microstructures can be a length of a natural number times the wavelength of light that induces surface plasmon on the metal microstructures.

The optical element can comprise a metal film provided with a plurality of micro-openings for the first group of metal microstructures or the second group of metal microstructures.

The metal film can comprise at least one element selected from the group consisting of gold, silver, platinum, copper and aluminum.

The micro-openings can be periodically disposed with a specific period B.

The period B can be a length of a natural number times the wavelength of light that induces surface plasmon on the micro-openings.

The present invention is directed to a sensor apparatus comprising: the optical element; a light source capable of irradiating the optical element with light; The present invention is directed to a detector capable of detecting transmitted light from the optical element; and a vessel holding an analyte.

The light source can be formed so as to be capable of irradiating light of the wavelength that induces surface plasmon on the metal microstructures or the metal film comprising the optical element.

The present invention is directed to a sensing method that utilizes the sensor apparatus, comprising the steps of: preparing an analyte; measuring as an optical spectrum 1 with the detector the transmitted light from the optical element obtained by irradiating the optical element with light from the light source; processing the optical element with the analyte; measuring as an optical spectrum 2 with the detector the transmitted light from the optical element obtained by irradiating the optical element which has been subjected to the processing, with light from the light source; and detecting the analyte by measuring the change between the optical spectrum 1 and the optical spectrum 2.

The analyte can be a biological molecule.

In the detecting step, the concentration of the analyte can be detected by measuring the magnitude of the change between the optical spectrum 1 and the optical spectrum 2.

The present invention is directed to a sensor apparatus comprising: the optical element; a light source capable of irradiating the optical element with light; a detector capable of detecting transmitted light from the optical element; and a vessel holding an analyte.

The light source can be formed so as to be capable of irradiating light of the wavelength that induces surface plasmon on the metal microstructures or the metal film comprising the optical element.

The present invention is directed to a sensing method that utilizes the sensor apparatus, comprising the steps of: preparing an analyte; measuring as an optical spectrum 1 with the detector the transmitted light from the optical element obtained by irradiating the optical element with light from the light source; processing the optical element with the analyte; measuring as an optical spectrum 2 with the detector the transmitted light from the optical element obtained by irradiating the optical element which has been subjected to the processing with light from the light source; and detecting the analyte by measuring the change between the optical spectrum 1 and the optical spectrum 2.

The analyte can be a biological molecule.

In the detecting step, the concentration of the analyte can be detected by measuring the magnitude of the change between the optical spectrum 1 and the optical spectrum 2.

An optical element according to the present invention is an optical element utilizing the localized surface plasmon resonance, including: a dielectric substrate; a first group of metal microstructures in which a plurality of metal microstructures is supported on the dielectric substrate in an in-plane direction of the substrate; and a second group of metal microstructures in which a plurality of metal microstructures is disposed in the in-plane direction, and each of the metal microstructures is partially exposed to the outside; wherein the first group of metal microstructures and the second group of metal microstructures are laminated so as to be separated from each other by 100 nm or more.

The optical element of the present invention can detect an analyte with a higher sensitivity and a higher precision than the conventional techniques.

Further features of the present invention will become apparent from the following description of exemplary embodiments with reference to the attached drawings.

BRIEF DESCRIPTION OF THE DRAWINGS

FIGS. 6A and 6B show schematic views illustrating the optical element of Example 2.

DESCRIPTION OF THE EMBODIMENTS

Optical Element

Figure 1:
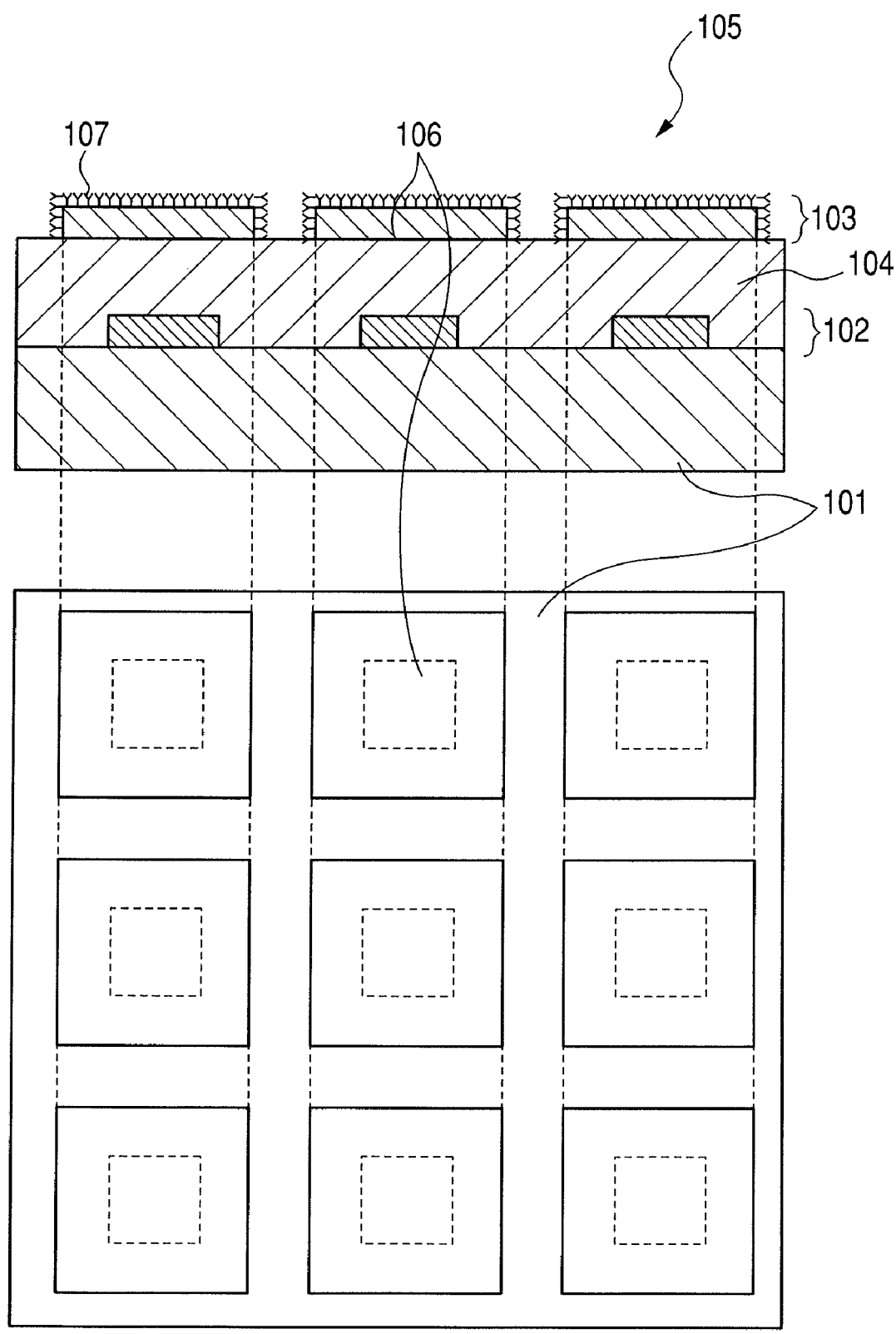
FIG. 1 shows a schematic view illustrating an embodiment of an optical element of the present invention.

The present invention relates to a technique for measurement sensitivity improvement in a method for evaluating an analyte on the basis of the change of the optical spectrum or the changes of other optical signals of metal microstructures or a metal film having micro-openings capable of inducing surface plasmon.

Hereinafter, the present invention will be described in more detail. Specifically, the optical element according to the present invention utilizing the localized surface plasmon resonance has the following features.

(1) The optical element has a group of metal microstructures in which a plurality of metal microstructures is supported on the dielectric substrate in an in-plane direction of the substrate (the first group of metal microstructure).

(2) The optical element has a group of metal microstructures in which one or more metal microstructures are disposed in the in-plane direction, and each of the metal microstructures is partially exposed to the outside (the second group of metal microstructure).

(3) The first group of metal microstructures and the second group of metal microstructures are laminated so as to be separated from each other by 100 nm or more.

Additionally, the groups of metal microstructures constituting the optical element may include a third group of metal microstructures other than the above-described first group of metal microstructures and the above-described second group of metal microstructures.

Here, the second group of metal microstructures is partially exposed to the outside. The possession of such exposed surface leads to a physical interaction or a chemical reaction with a specific substance or a specific ambient environment, and hence leads to the changes of the properties of the surface plasmon excited in the group of metal microstructures.

Additionally, when the second group of metal microstructures is disposed above the first group of metal microstructures, the distance between the first group of metal microstructures and the second group of metal microstructures means the distance between the uppermost surface of the first group of metal microstructures and the lowermost surface of the second group of metal microstructures.

On the other hand, when the first group of metal microstructures is disposed above the second group of metal microstructures, the distance between the first group of metal microstructures and the second group of metal microstructures means the distance between the lowermost surface of the first group of metal microstructures and the uppermost surface of the second group of metal microstructures.

The surfaces on each of which the metal microstructures constituting each of these groups of metal microstructures are disposed may be parallel or nonparallel to each other.

The above-described structure (2) enables the second group of metal microstructures to undergo a physical interaction or a chemical reaction with a specific substance or a specific ambient environment; as compared to before the occurrence of the physical interaction or the chemical reaction, after the occurrence of the physical interaction or the chemical reaction, the occurrence of the change of the dielectric constant of the environment surrounding the group of metal microstructures can be detected as the change of the optical spectrum.

The above-described structure (3), namely, the laminated structure leads to interaction between the first group of metal microstructures and the second group of metal microstructures. Consequently, the peak position, peak size and peak shape of the optical spectrum can be changed between before and after the detection of the analyte.

On the other hand, since the first group of metal microstructure and the second group of metal microstructure are laminated with a distance of 100 nm or more from each other, the interaction between the first and second groups of metal microstructures through the near field generated by the irradiation of the optical element with light can be prevented. Consequently, a high-sensitivity sensing can be achieved.

In other words, in the present invention, by controlling the spectra of the respective groups of metal microstructures in the optical element, the optical spectrum of the whole optical element can be made to have a desired shape. Additionally, the way of the spectral change of the optical element corresponding to the change of the dielectric constant in the environment surrounding the optical element can be varied by varying the element structure as described above.

Hereinafter, the involved principle is described in detail.

For example, when a plurality of first to n-th groups of metal microstructures is sequentially laminated, the optical spectra obtained by irradiating the respective groups of metal microstructures with light, before attachment of the analyte, are denoted by $I_1, I_2, \ldots I_n$. Thus, the spectrum of the whole optical element represented as a combination of these optical spectra is given by the product of the optical spectra of the respective groups of metal microstructures as represented by the following formula (I):

$$I_1 \times I_2 \times \ldots I_n \quad (I)$$

Here, for example, when the dielectric constant of the environment surrounding the first group of metal microstructures is changed by the attachment of an analyte, the optical spectrum obtained by irradiating the first group of metal microstructures with light is changed from $I_1$ to $I_1{}^*$.

Consequently, the spectrum of the whole optical element represented as a combination of these optical spectra is given by the product of the optical spectra of the respective groups of metal microstructures as represented by the following formula (II):

$$I_1{}^* \times I_2 \times \ldots I_n \quad (II)$$

Consequently, the detection of the analyte by the optical element can be learned by the spectral difference represented by formula (II)–formula (I).

Here, in some cases, the optical spectra corresponding to the respective groups of metal microstructures are only shifted in peak position by the attachment of an analyte. However, in the present invention, the product of the optical spectra from the plurality of groups of metal microstructures is the spectrum of the whole optical element. Accordingly, by varying the optical spectra from the respective groups of metal microstructures, the peak position, peak size and peak shape of the optical spectrum of the whole optical element can be controlled so as to be the desired position, size and shape.

Although the above description presents a case where the analyte attaches to the first group of metal microstructures, even a case where the analyte attaches to a plurality of groups of metal microstructures (the spectra of the groups attached with the analyte are varied) can be understood as described above. For example, when the analyte attaches to the first and n-th groups of metal microstructures, the optical spectra of the first and n-th groups of metal microstructures are changed from $I_1$ and $I_n$ to $I_1{}^*$ and $I_n{}^*$, respectively.

Consequently, the spectrum of the whole optical element represented as a combination of these optical spectra is given by the product of the optical spectra of the respective groups of metal microstructures as represented by the following formula (III):

$$I_1{}^* \times I_2 \times \ldots I_n \quad (III)$$

Consequently, the detection of the analyte by the optical element can be learned by the spectral difference represented by formula (III)–formula (I).

Examples of a metal microstructure include rectangular, spherical and other microstructures that have flat or curved surfaces.

More preferably, it is recommended that each of the groups of metal microstructures includes a plurality of metal microstructures (metal particles) that are the same in shape. In this case, the metal microstructures constituting each of the groups of metal microstructures are metal particles that are the same in shape, but the metal microstructures constituting different groups of metal microstructures may be the same or different in shape. By making the metal microstructures constituting each of the groups of metal microstructures be metal particles that are the same in shape, the control of the shape and peak of the optical spectrum is more facilitated.

Furthermore preferably, it is recommended that all the metal microstructures constituting the optical element have the same shape. By making all the metal microstructures have the same shape, the optical element of the present invention can carry out sensing with a higher sensitivity.

The size of each of the metal microstructures is required to be smaller than the wavelength of the light applied to the optical element.

The metal microstructures constituting each of the groups of metal microstructures are preferably periodically disposed with a specific period A in each group.

By periodically disposing the metal microstructures with a specific period A as described above, the control of the shape and peak of the optical spectrum is more facilitated.

(a) The period A is preferably a length of a natural number times the wavelength of the light that induces surface plasmon on the metal microstructures. It is to be noted that "the wavelength of the light that induces surface plasmon" as referred to herein represents an effective wavelength that takes account of the effective refractive index in the vicinity of the surface of the metal microstructures on which the surface plasmon is induced.

By setting the period A to be a length of a natural number times the wavelength of the light that induces surface plasmon resonance on the individual metal microstructures, the confinement effect of the light that induces plasmon resonance on each of the surfaces of the groups of metal microstructures can be intensified.

The period A is preferably 10 nm or more and 10000 nm or less, more preferably 200 nm or more and 2000 nm or less, and furthermore preferably 400 nm or more and 1000 nm or less.

The respective groups of metal microstructures may be disposed so as to be parallel to each other or so as to be nonparallel to each other. A fabrication procedure to yield a parallel disposition is easier. On the other hand, in a nonparallel disposition, the deviation angle from the parallel direction serves as a parameter to affect the optical properties, and hence such nonparallel disposition enables easier control of the optical properties. A nonparallel disposition structure may be fabricated, for example, by using a quartz substrate having a wedge-shaped cross section.

(b) When all the groups of metal microstructures are disposed so as to be parallel to each other, the distance between the adjacent groups of metal microstructures is preferably set at a length of a natural number times the wavelength of the light that induces surface plasmon on the metal microstructures. In this case, "the wavelength of the light that induces the surface plasmon" means the light wavelength in between the adjacent groups of metal microstructures.

By setting the distance between the adjacent groups of metal microstructures to be a natural number times the wavelength of the light that induces surface plasmon resonance, the confinement effect of the light in the whole optical element inclusive of the gaps between these groups can be intensified. Consequently, a band narrowing of the peak width in the whole optical element is enabled.

By possessing a structure in conformity with the above descriptions (a) and (b), the confinement effect of the light in the whole optical element is further intensified. Consequently, a further band narrowing of the peak width in the whole optical element is enabled.

The above-described period A and the above-described distance between the adjacent groups of metal microstructures each are not necessarily required to be exactly a natural number times the wavelength of the light that induces the surface plasmon resonance. However, in principle, the period A and the distance each preferably fall within of the order of the above-described plasmon resonance width (half width of approximately 100 nm) from the natural number times the above-described wavelength.

Here, the distance between the first group of metal microstructures and the second group of metal microstructures is required to be 100 nm or more, but is also required to be not too large. The reasons for this are as follows.

The groups of metal microstructures each are finite in area, and scattered light is generated from the metal microstructures. Consequently, the increase of the distance between the groups of metal microstructures increases the proportion of the scattered light, from one of the groups of metal microstructures, that does not reach the adjacent other group of metal microstructures and is dissipated.

Additionally, when the spacing between the metal microstructures in a group of metal microstructures is larger than the wavelength of the incident light, diffracted light beams are generated. Also for the purpose of suppressing the dissipation, from the optical element of the present invention, of these diffracted light beams to a lowest possible level, the distance between the groups of metal microstructures is preferably the smaller the better.

Additionally, when the space between the above-described groups of metal microstructures is filled with a medium, the increase of the distance between the groups increases the propagation loss in the medium.

Additionally, when the above-described groups of metal microstructures each have a high reflectance to generate reflected light, the space sandwiched between the above-described groups of metal microstructures forms a kind of resonator. In this case, as a result of a characteristic of the resonator, sharp peaks appear in the transmission spectrum of the resonator, and sharp dips appear in the reflectance spectrum of the resonator. The peaks and dips in these spectra are gradually increased in number and become extremely sharp with the increase of the length of the resonator. Accordingly, when the above-described distance between the groups of metal microstructures is increased, a large number of sharp peaks and sharp dips appear in the optical spectrum of the whole element. Consequently, the optical spectrum of the whole element unpreferably becomes quite different from the product of the optical spectra respectively obtained from the above-described groups of metal microstructures with each group in a form of a single layer. In other words, for the purpose of making as wide as possible the distances between the sharp dips and the distances between the sharp peaks and reducing the number of the peaks and dips in a target wavelength region in the spectrum, the length of the resonator is preferably the shorter the better. In other words, the distance between the above-described groups of metal microstructures is preferably the shorter the better.

In this connection, it is considered that the free spectral range (FSR) of the resonator modes based on the above-described Fabry-Perot resonator in the visible light region is made to be of the order of 100 nm or more that is a typical LSPR spectral width. In this case, on the basis of the assumption that the refractive index of the space between the groups of metal microstructures is unity, the mutual distance between the above-described groups of metal microstructures is preferably set at 1 μm or less. Additionally, when the refractive index is n, the mutual distance is preferably 1/n or less this value.

The first group of the metal microstructures is supported by a dielectric substrate. The term "supporting" as referred to herein may include either a case where the first group of metal microstructures is disposed on the dielectric substrate or a case where the first group of metal microstructures is embedded in the dielectric substrate. Such disposition of the first group of metal microstructures on the substrate facilitates the transmission of light in the optical element, and thereby enables to carry out sensing with a higher precision. The group of metal microstructures may be disposed either on one side of the dielectric substrate or on both sides of the dielectric substrate.

There can be adopted an optical element which includes a metal film provided with a plurality of micro-openings in place of the first group of metal microstructures or the second group of metal microstructures. Typically, the localized surface plasmon is generated in the interface between a metal and a dielectric, the metal film provided with micro-openings can also display the same function as displayed by the first group of metal microstructures or the second group of metal microstructures.

In this case, the metal film provided with micro-openings and the group of metal microstructures are laminated so as to be separated with the distance of 100 nm or more on the basis of the above-described reasons.

Additionally, the metal film preferably includes at least one element selected from the group consisting of gold, silver, platinum, copper and aluminum.

Additionally, the size of the micro-opening is equal to or less than the measurement wavelength used in the optical measurement.

Hereinafter, description is made on the embodiments of the present invention by using examples, but the description does not impose any restriction on the present invention.

Here, for example, description is made on a case where an antigen is used as a target substance (analyte) and an antigen-antibody reaction is implemented.

First Embodiment

FIG. 1 shows a schematic view illustrating an embodiment of the present invention. First, the structure of an optical element 105 of the present embodiment is described. Specifically, a first group 102 of metal microstructures was disposed on the surface of a dielectric substrate 101. Additionally, an interlayer film 104 is formed on the first group 102 of metal microstructures, and a second group 103 of metal microstructures is disposed on the interlayer film 104.

Here, the distance between the group 102 of metal microstructures and the group 103 of metal microstructures is required to be of such an order that the group 102 of metal microstructures and the group 103 of metal microstructures do not interact through the generated near field when the optical element 105 is irradiated with the measurement light. The distance required for this purpose is 100 nm or more.

At least part of the gap (space) between the respective groups of metal microstructures preferably includes a dielectric. Such inclusion of a dielectric in at least part of the space between the respective groups facilitates the transmission of light in the optical element, and thereby enables to carry out sensing with a higher precision.

In the present embodiment, the first group 102 of metal microstructures and the second group 103 of metal microstructures are made of Au. Here, the material constituting the metal microstructures is not limited to Au, and no particular constraint is imposed the material as long as the material is a conductive material. The material is preferably a metal small in dielectric loss. It is preferable to include, as a metal among such metals, at least one element selected from the group consisting of gold, silver, platinum, copper and aluminum. Possible examples of a form including two or more of these elements include alloys and mixtures thereof. Constitution of the metal microstructures with these metals enables to carry out sensing with a higher precision.

Additionally, in the present embodiment, the dielectric substrate 101 and the interlayer film 104 are made of quartz. In the optical element of the present invention, when the dielectric substrate 101 and the interlayer film 104 are used, the materials constituting the dielectric substrate 101 and the interlayer film 104 may be the same or different from each other. However, the materials constituting the dielectric substrate 101 and the interlayer film 104 are preferably such materials that are high in transparency in the measurement wavelength used for the optical measurement.

In the present embodiment, the metal microstructures 106 constituting the second group 103 of metal microstructures are partially exposed to the outside of the interlayer film 104, and the exposed surface of the metal microstructures 106 is modified with an antibody 107.

Then, an antigen-antibody reaction is made to occur around the metal microstructures 106, and the optical spectral signals before and after the occurrence of the antigen-antibody reaction are compared with each other.

Figure 2:
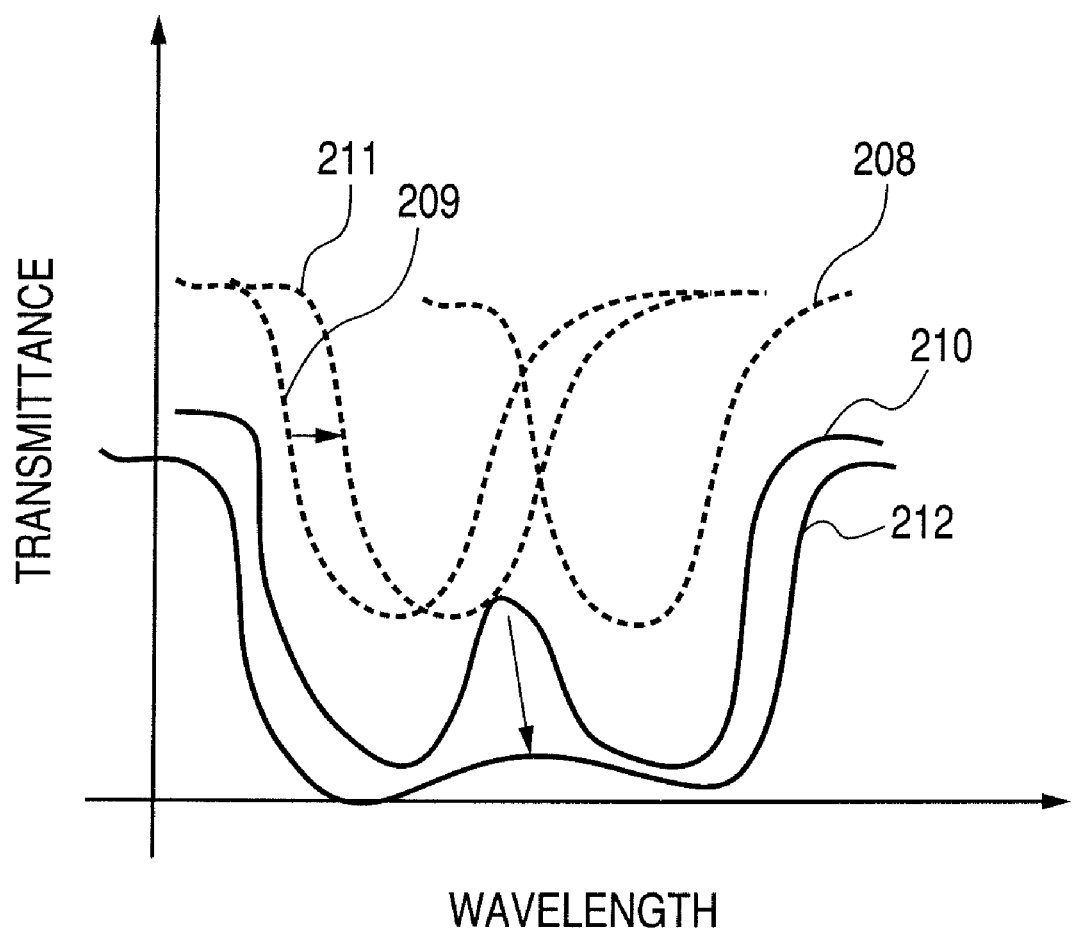
FIG. 2 shows the measurement results for an embodiment of the optical element of the present invention.
Figure 3A:
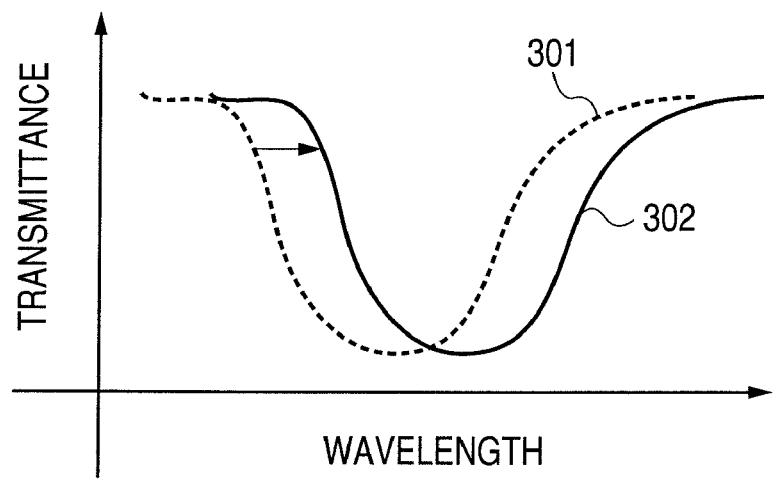
FIGS. 3A and 3B show a schematic chart and a schematic view illustrating a conventional sensing technique.
Figure 3B:
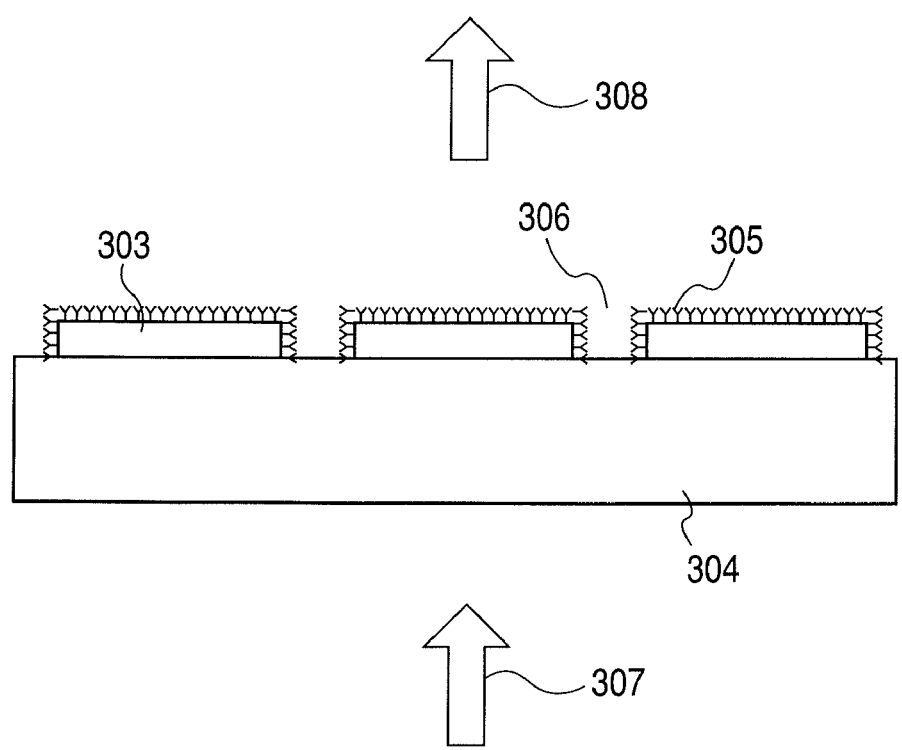

FIG. 2 shows a chart illustrating the optical spectral change between before and after the antigen-antibody reaction. First, the transmission spectra, before the implementation of the antigen-antibody reaction, of the first group 102 of metal microstructures and the second group 103 of metal microstructures are measured.

In FIG. 2, the transmission spectrum of the first group 102 of metal microstructures is shown as the transmission spectrum 208, and the transmission spectrum of the second group 103 of metal microstructures is shown as the transmission spectrum 209.

Accordingly, when a spectrum is measured by arranging the measurement system in such a way that the measurement light transmits both of these groups of metal microstructures, the spectrum measured for the whole optical element is the transmission spectrum 210 before the reaction.

The transmission spectrum 210 before the reaction is the product of the transmission spectrum 208 and the transmission spectrum 209.

Next, the antigen-antibody reaction is made to occur on the surface of the second group 103 of metal microstructures, so as to lead to a state in which the antigen and the antibody are bonded to each other on the surface of the metal microstructures. In this state, the occurrence of the antigen-antibody reaction changes the dielectric constant of the environment surrounding the second group 103 of metal microstructures.

Consequently, as illustrated in FIG. 2, only the transmission spectrum 209 is changed into the transmission spectrum 211. Accordingly, the spectrum measured, after the antigen-antibody reaction, for the whole optical element is the transmission spectrum 212 after the reaction.

Similarly to the above description, the transmission spectrum 212 after the reaction is the product of the transmission spectrum 208 and the transmission spectrum 211.

As describe above, the spectrum measured for the whole optical element is changed from the transmission spectrum 210 before the reaction to the transmission spectrum 212 after the reaction on going from before to after the antigen-antibody reaction. This change generally induces not only the spectral peak wavelengths but other parameters such as the peak heights, and hence enables a high-sensitivity and high-precision measurement of the change of the dielectric constant of the environment surrounding the optical elements.

Here, in the above-described embodiment, among the plurality of groups of metal microstructures included in the optical element, only one group of metal microstructures was exposed on the surface of the optical element. And, only the exposed group of metal microstructures provides a change of the transmission spectrum thereof due to the change of the dielectric constant of the environment surrounding the optical element. However, one or two or more exposed groups of metal microstructures may be adopted. Alternatively, all the groups of metal microstructures constituting the optical element may be exposed.

Additionally, in the optical element of the present invention, the number of the surface-exposed groups of metal microstructures and the shapes of the metal microstructures constituting the layers concerned can be appropriately controlled. Such control enables the control of the shape of the transmission spectrum of the whole optical element, and the control of the change of the transmission spectrum caused by the change of the dielectric constant of the environment surrounding the optical element. Consequently, the spectral shape and the spectral change enabling high-sensitivity and high-precision sensing can be developed.

Second Embodiment

Figure 8A:
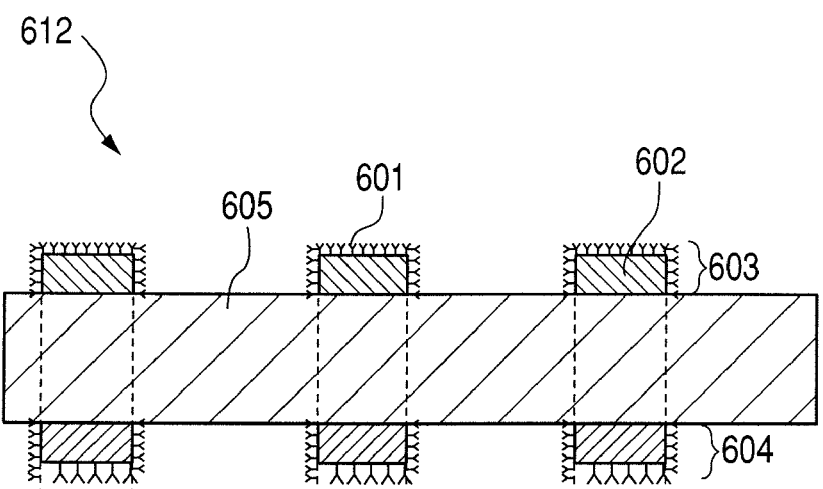
FIGS. 8A and 8B show schematic views illustrating an embodiment of an optical element of the present invention and the measurement results thereof.
Figure 8B:
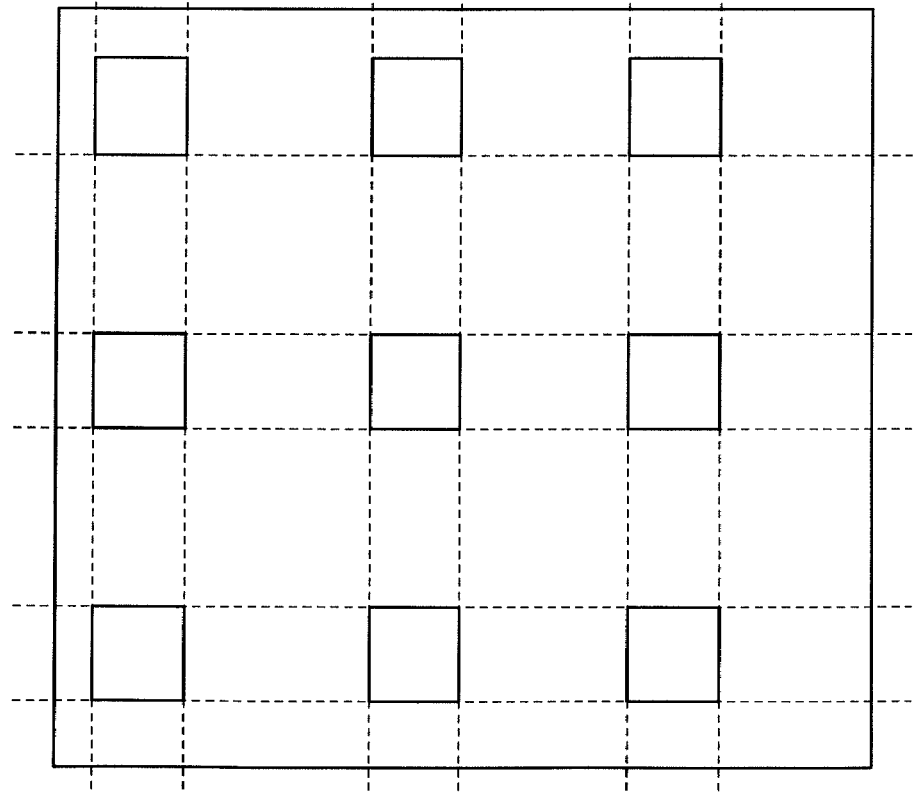

FIGS. 8A and 8B illustrate another examples of an optical element of the present invention. In the optical element, as illustrated in FIGS. 8A and 8B, a second group 603 of metal microstructures including metal microstructures 602 and a first group 604 of metal microstructures are disposed on both sides of a dielectric substrate 605. Additionally, the surface of the metal microstructures 602 constituting the respective groups of metal microstructures is modified with an antibody 601.

Figure 9:
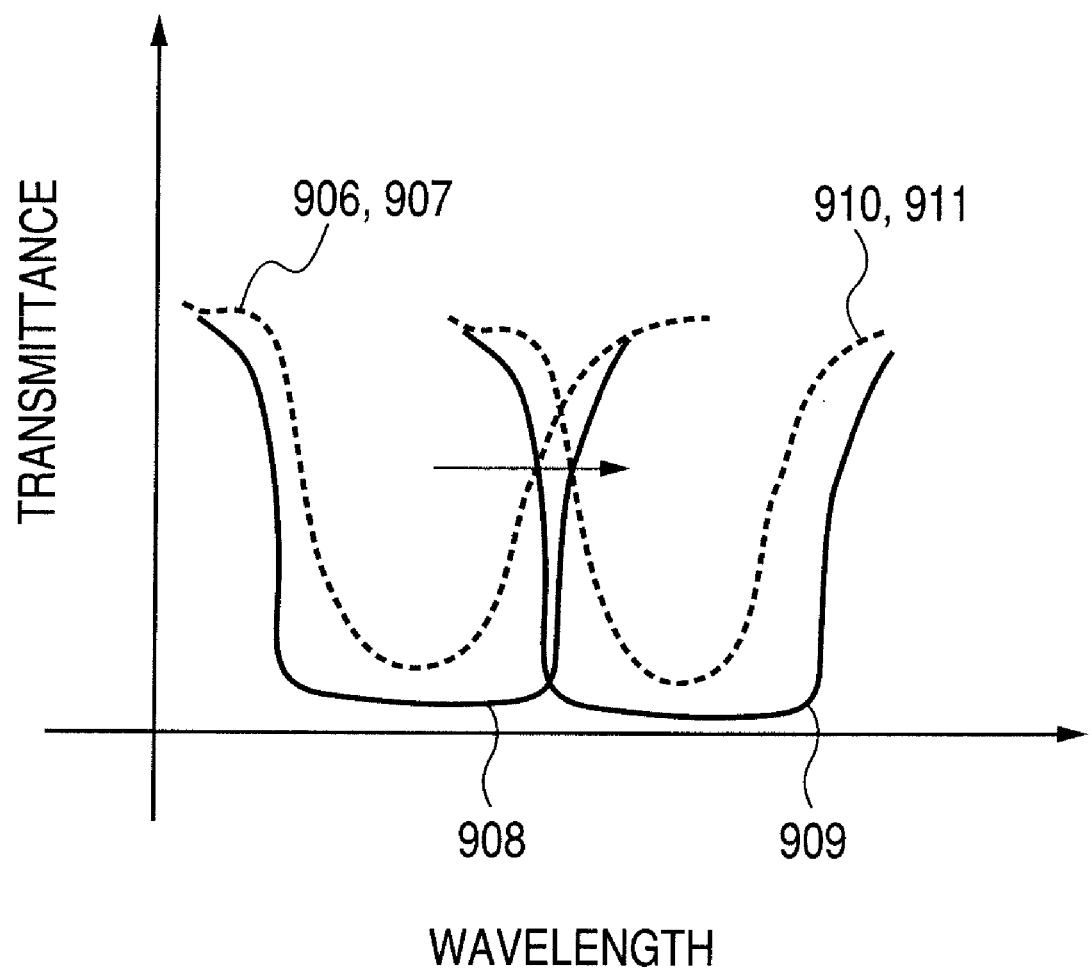
FIG. 9 shows a chart showing the measurement results for an embodiment of the optical element of the present invention.

In the above optical element, when the transmission spectra of the respective groups of metal microstructures are the same, the transmission spectra of each of the groups and the whole optical element are as illustrated in FIG. 9. In other words, the transmission spectrum of the second group 603 of metal microstructures is the transmission spectrum 906, the transmission spectrum of the first group 604 of metal microstructures is the transmission spectrum 907, and the transmission spectrum of the whole optical element is the transmission spectrum 908 before the reaction.

Here, when the antigen-antibody reaction is made to occur in the environment surrounding the optical element 612, the transmission spectrum of the second group 603 of metal microstructures becomes the transmission spectrum 910, and the transmission spectrum of the first group 604 of metal microstructures becomes the transmission spectrum 911. Because the transmission spectrum of the whole optical element 612 is the product of the transmission spectrum 910 and the transmission spectrum 911, the transmission spectrum of the whole optical element becomes the transmission spectrum 909 after the reaction. Consequently, as the transmission spectrum 909 after the reaction, such a spectral shape having a steep portion as illustrated in the figure can be actualized.

As described above, in the case of the optical element shown in FIG. 8A, the spectral shape manifesting the change of the transmission spectrum, in particular, the maximum slope angle of the spectrum becomes steep. Accordingly, measurement utilizing the wavelength region where the spectrum exhibits steep change enables high-sensitivity and high-precision sensing.

Third Embodiment

FIGS. 6A and 6B illustrate another embodiment of the present invention. The optical element of this embodiment includes a metal film having a plurality of micro-openings in place of the second group of metal microstructures.

Alternatively, the optical element may include a metal film having a plurality of micro-openings in place of the first group of metal microstructures. Furthermore, in the optical element, both of the first group of metal microstructures and the second group of metal microstructures may be respectively replaced with metal films each having a plurality of micro-openings.

These micro-openings are preferably the same in shape. When this is the case, the micro-openings formed on the metal film are mutually the same in shape.

When both of the groups of metal microstructures are replaced with metal films, the shapes of the micro-openings in the respective metal films are mutually the same in shape or different in shape from each other.

The same shape shared by the micro-openings facilitates the control of the optical properties of the transmitted light from the optical element. Typically, the micro-openings are rectangular in shape, but are not limited to this shape.

The plurality of micro-openings provided in the metal film is preferably periodically disposed with a specific period B. Such periodic disposition of the micro-openings with a specific period B further facilitates the control of the shape and peaks of the optical spectrum.

The period B is preferably a length of a natural number times the wavelength of the light that induces surface plasmon in the micro-openings. It is to be noted that "the wavelength of the light that induces surface plasmon" as referred to herein represents an effective wavelength that takes account of the effective refractive index in the vicinity of the micro-openings in which the surface plasmon is induced.

By setting the period B to be a length of a natural number times the wavelength of the light that induces surface plasmon resonance in the respective micro-openings, the confinement effect of the light that induces plasmon resonance on each of the surfaces of the groups of metal microstructures can be intensified.

The period B is preferably 100 nm or more and 10000 nm or less, more preferably 200 nm or more and 2000 nm or less, and furthermore preferably 400 nm or more and 1000 nm or less.

(Sensor Apparatus)

Figure 5A:
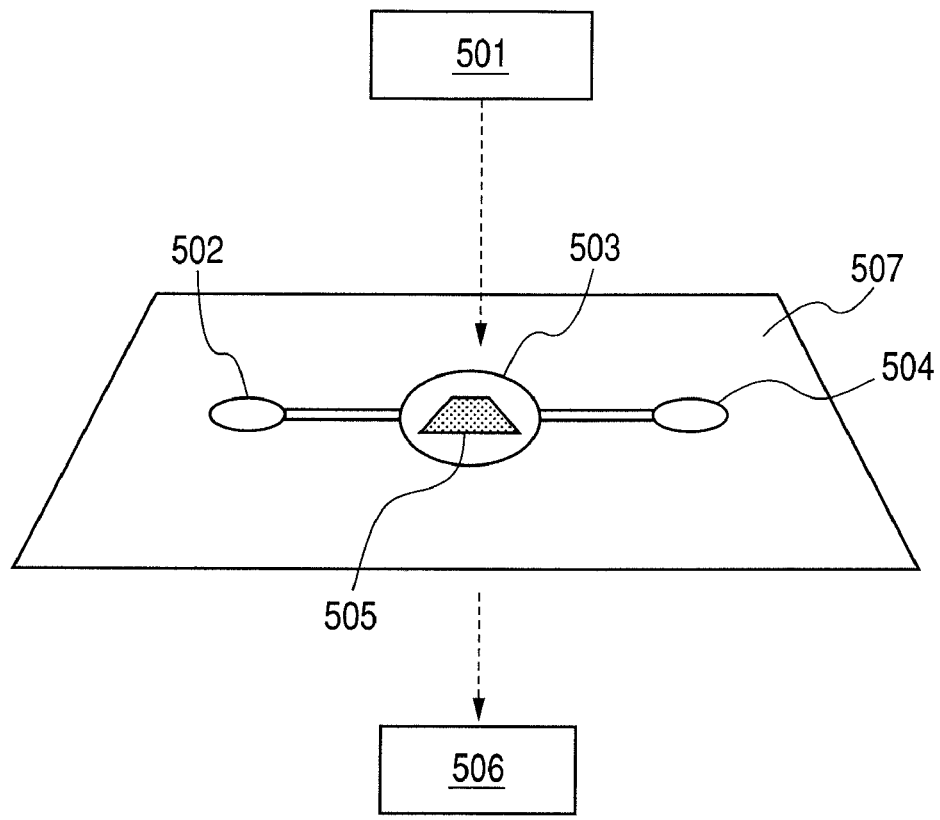
FIGS. 5A and 5B show a view and a chart illustrating the sensor apparatus and the measurement results of Example 1, respectively.
Figure 5B:
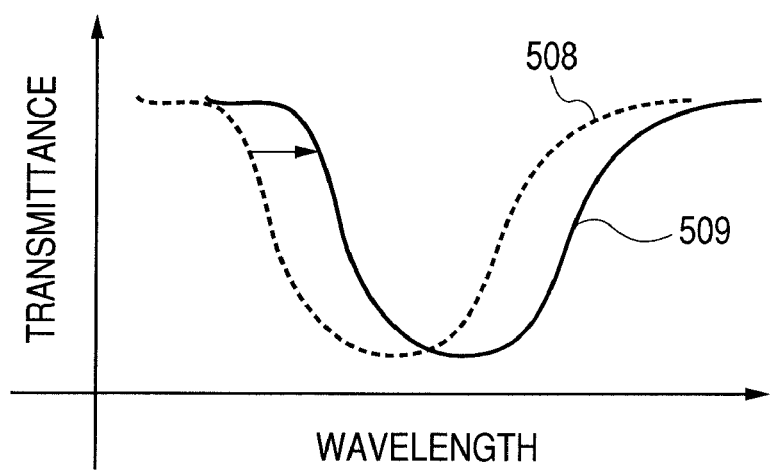

A sensor apparatus of the present invention includes the above-described optical element, a light source capable of irradiating the optical element with light, a detector capable of detecting the light from the optical element and a vessel holding an analyte. FIGS. 5A and 5B schematically illustrate an example of the sensor apparatus.

In the sensor apparatus, an optical element 505 including the group(s) of metal microstructures or the metal film(s) according to the present invention is disposed, and a light source 501 is provided above the optical element 505. Additionally, on the side opposite to the light source 501, a spectroscopic detector (detector) 506 is provided so as to be capable of detecting the transmitted light from the optical element 505. Additionally, the analyte is held in the vessel (not shown), and can be made to flow into a reaction well 503 through an injection opening 502. The analyte fraction that has not attached to the optical element 505 is discharged through a discharge opening 504.

A liquid other than the analyte such as a cleaning liquid can also be made to flow in the region including the injection opening 502-the reaction well 503-the discharge opening 504. Additionally, the light source is preferably constructed so as to be capable of irradiating such light having the wavelength that induces the surface plasmon on the metal microstructures or in the micro-openings.

(Sensing Method)

A sensing method of the present invention utilizes the above-described sensor apparatus, and includes the following steps of: preparing an analyte; measuring as an optical spectrum 1 with the detector the transmitted light from the optical element obtained by irradiating the optical element with light from the light source; processing the optical element with the analyte; measuring as an optical spectrum 2 with the detector the transmitted light from the optical element obtained by irradiating the optical element, having been subjected to the processing, with light from the light source; and detecting the analyte by measuring the change between the optical spectrum 1 and the optical spectrum 2.

Specifically, the sensing method can utilize the method of Example 1 that uses the sensor apparatus shown in FIGS. 5A and 5B. Additionally, a biological molecule can be used as an analyte. The sensing method of the present invention is capable of detecting even a small amount of a biological molecule with a high sensitivity, and hence is an effective method. It is preferable to detect the concentration of the analyte by measuring the magnitude of the change between the optical spectra 1 and 2 in the above-described detection step. In this case, by using a sample having a known concentration, the relation between the concentration and the magnitude of the spectral change of the sample is beforehand determined as a calibration curve. By comparing the magnitude of the change between the actually measured optical spectra 1 and 2 with the calibration curve, the concentration of the analyte can be detected.

(Method for Preparing Optical Element)

The method for preparing a first optical element of the present invention includes the following steps of: preparing a dielectric substrate; forming a conductive film A on the dielectric substrate; forming on the dielectric substrate by patterning the conductive film A the first group of metal microstructures including a plurality of metal microstructures disposed on the dielectric substrate; forming a dielectric film and a conductive film B in this order on the first group of metal microstructures formed on the dielectric substrate; and forming by patterning the conductive film B the second group of metal microstructures including a plurality of metal microstructures disposed on the dielectric film.

In the preparation method, first the dielectric substrate is prepared. Next, the conductive film A is formed on the dielectric substrate by using a sputtering apparatus, a CVD apparatus or a vapor deposition apparatus. Next, the conductive film A is subjected to patterning by using a focused ion beam (FIB) processing apparatus, or by using, after applying resist, an electron beam printing apparatus or an exposure apparatus such as a stepper and using a dry etching process or a lift off process. The patterning enables to form a pattern shape so as to have a desired size and a desired spacing. Thus formed is the first group of metal microstructures including the plurality of metal microstructures disposed on the dielectric substrate.

Next, the dielectric film is formed on the above pattern by using a sputtering apparatus, a CVD apparatus or a SOG apparatus. Thereafter, the conductive film B is formed on the dielectric film by using a sputtering apparatus, a CVD apparatus or a vapor deposition apparatus. Next, the conductive film B is subjected to patterning by using a focused ion beam (FIB) processing apparatus, or by using, after applying resist, an electron beam printing apparatus or an exposure apparatus such as a stepper and using a dry etching process or a lift off process. The patterning enables to select a desired pattern shape. Thus formed is the second group of metal microstructures including the plurality of metal microstructures disposed on the dielectric film.

In the preparation method, by repeating, according to need, such formation as described above of a dielectric film and a group of metal microstructures, an optical element including desired dielectric films and desired groups of metal microstructures can be prepared.

Additionally, in the preparation method, by repeating, according to need, such formation as described above of a dielectric film and the above-described metal film, an optical element including desired dielectric films and desired above-described metal films can also be prepared.

The method for preparing a second optical element of the present invention includes the following steps of: forming metal films including a plurality of micro-openings by repeating two or more times the following steps from (1) to (4), namely, the steps of (1) preparing a dielectric substrate, (2) forming a conductive film C on the dielectric substrate, (3) forming in the conductive film C a plurality of micro-openings by subjecting the conductive film C to patterning, and (4) removing the dielectric substrate so as for the dielectric substrate to remain in directly beneath the periphery of the metal film including the plurality of micro-openings; and laminating a metal film provided with a dielectric substrate in directly beneath the two or more peripheries formed by the step of forming the metal films.

In the preparation method, first the dielectric substrate is prepared (step (1)). Next, the conductive film C is formed on the dielectric substrate by using a sputtering apparatus, a CVD apparatus or a vapor deposition apparatus (step (2)).

Next, the plurality of micro-openings is formed in the conductive film C by subjecting the conductive film C to patterning by using a focused ion beam (FIB) processing apparatus, or by using, after applying resist, an electron beam printing apparatus or a stepper and using a dry etching process or a lift off process. By the patterning, the metal film including micro-openings is formed on the dielectric substrate (step (3)). In this case, the pattering enables to form a pattern shape having a desired size and a desired spacing.

Next, a resist is patterned on the backside of the dielectric substrate, and thereafter the dielectric substrate is removed by dry etching so as to remain in directly beneath the periphery (the outside of the area surrounding the plurality of micro-openings) of the metal film including the plurality of micro-openings (step (4)). Here, the etching mask is not limited to a resist, but may be a mask made of a metal or other materials.

By repeating the above-described steps from (1) to (4), a desired number of metal films are prepared. Next, these metal films each provided with a dielectric substrate in directly beneath the periphery are laminated and fixed. The fixing method may be a method of fixing by using a fixing jig, or other fixing or bonding methods.

EXAMPLES

Hereinafter, the present invention is described with reference to Examples, but these examples do not impose any constraint on the scope of the present invention.

Example 1

Figure 4A:
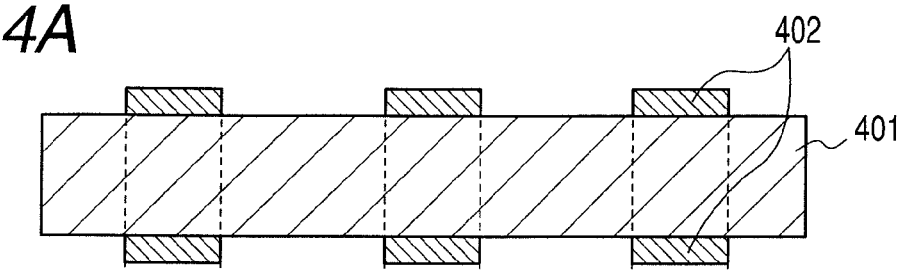
FIGS. 4A, 4B and 4C show schematic views illustrating an embodiment of the optical element of the present invention.
Figure 4B:
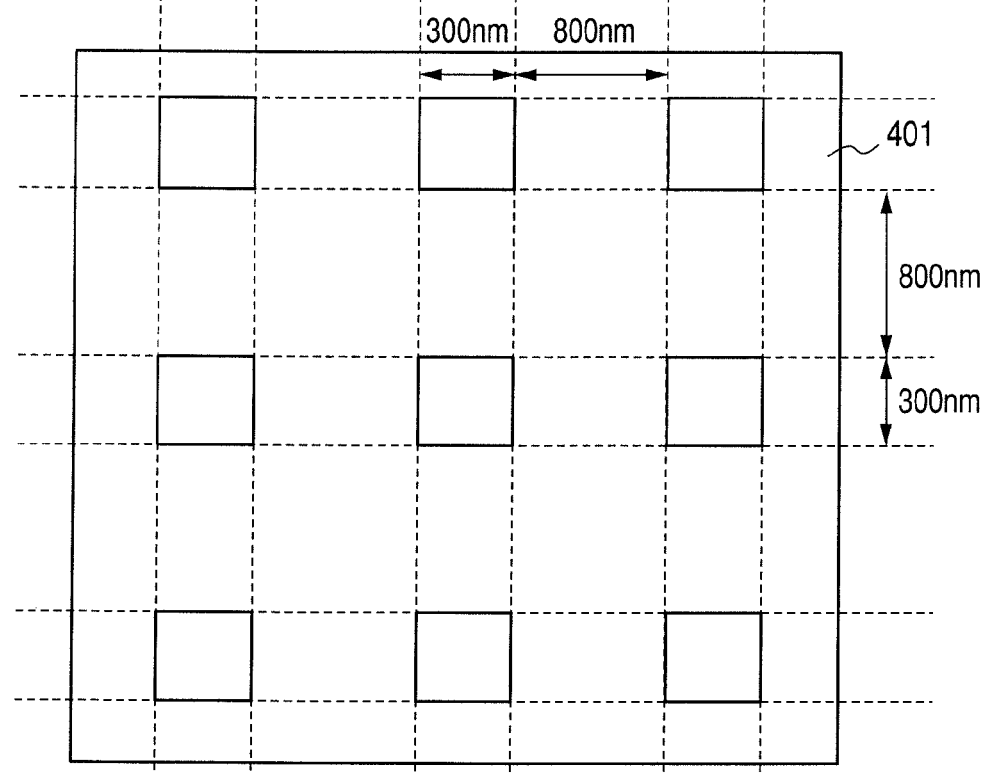
Figure 4C:
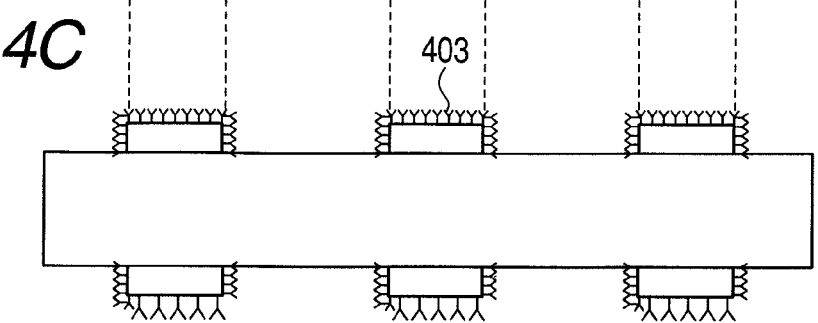

FIGS. 4A, 4B and 4C illustrate a sensor apparatus and a sensing method using an optical element of the present invention. In the optical element, on both sides of a support (a dielectric substrate) 401, two groups of metal microstructures each including a plurality of metal particles (metal microstructures) 402 are disposed, and these two groups of metal microstructures are exposed to the outside. Additionally, as illustrated in FIG. 4B, the plurality of metal particles is such that a plurality of square metal particles (metal microstructures) with a side of approximately 300 nm are disposed on one and the same surface and in a square lattice shape with a spacing of approximately 800 nm between the respective metal particles.

The support 401 is approximately 550 µm in thickness and is made of quartz. The two groups of metal microstructures are separated by 550 µm from each other. The material for the support 401 is not limited to quartz, and is preferably a material having a high transmittance in the wavelength region for measuring the optical spectrum. Additionally, the thickness of the support is also not limited to the above-described value.

The metal particles 402 on the support 401 each are an Au thin film of approximately 20 nm in thickness. The thickness of the metal particles 402 is not limited to this value. The material for the metal particles 402 is also not limited to Au, and is preferably a material capable of generating the surface plasmon resonance; in particular, preferable is a metal small in dielectric loss such as Ag, Cu, Pt and Al. Additionally, the material for the metal particles 402 may be other metallic substances such as semiconductors.

Next, the surface of the metal particles 402 is modified with an antibody. Examples of the method for modifying the surface of the metal particles 402 include the following method: for example, an anti-AFP (α-fetoprotein) antibody can be immobilized on the Au surface of the metal particles 402; in this case, an ethanol solution of 11-mercaptoundecanoic acid having a thiol group is placed dropwise with a spotter or the like on the Au surface of the metal particles 402; thus, the carboxyl groups are exposed on the surface of the metal particles.

Next, in the same manner as described above, an aqueous solution of N-hydroxysulfosuccinimide and an aqueous solution of 1-ethyl-3-[3-dimethylamino]propyl carbodiimide hydrochloride are placed dropwise with a spotter or the like on the Au surface of the metal particles 402, in particular, on the reaction area. Thus, the succinimide groups are exposed on the surface of the metal particles.

Next, the surface of the metal particles is reacted with streptavidin to be modified with streptavidin. Then, biotinylated anti-AFP antibody is immobilized on the microparticles modified with streptavidin. Consequently, as illustrated in FIG. 4C, the surface of the metal particles 402 is turned into the state modified with the antibody 403, and the surface of the metal particles is turned into the surface capable of reacting with an antigen.

Next, by using a sensor apparatus provided with an optical element in which, as describe above, the antibody 403 is immobilized on the surface of the metal particles, the antigen-antibody reaction is implemented and the measurement of the optical spectrum is carried out. The measurement is carried out by using a sensor apparatus having a configuration illustrated in FIGS. 5A and 5B.

In the sensor apparatus, the optical element 505 according to the present invention is disposed in the reaction well 503. In the sensor apparatus, a phosphate buffer solution is injected from the injection opening 502 and the phosphate buffer solution is filled in the reaction well 503. Then, the light from the light source 501 is introduced into the optical element 505, and the scattered light from the optical element 505 is measured spectroscopically with the spectroscopic detector 506 to measure the optical spectrum 508 before the reaction. Here, a tungsten lamp was used as the light source 501, but the light source is not limited to this lamp.

Next, an analyte containing AFP is injected from the injection opening 502, and is made to flow into the interior of the reaction well 503 so as for AFP to be captured on the optical element 505. Thereafter, the analyte fraction that has not been captured by the optical element is discharged from the discharge opening 504, and thereafter the phosphate buffer solution is injected from the injection opening 502 to clean the interior of the reaction well 503. Finally, the phosphate buffer solution is filled in the reaction well 503.

Next, the light from the light source 501 is introduced into the optical element 505, and the transmitted light from the optical element 505 is measured spectroscopically with the spectroscopic detector 506 to measure the optical spectrum 509 after the reaction.

Then, by comparing the optical spectrum 508 before the reaction with the optical spectrum 509 after the reaction (FIG. 5B), the peak shift magnitude due to the localized plasmon resonance is obtained, and the concentration of the target substance is detected from the obtained shift magnitude. In this case, by beforehand obtaining the relation between the signal value and the concentration by using the AFP solutions each having a known concentration, the concentration of the measured analyte can be obtained.

As describe above, use of the optical element of the present invention enables a high-sensitivity measurement. In present Example, the metal particles were square thin films, but are not limited to such square thin films; the metal particles have only to be structures capable of inducing LSPR.

Additionally, in present Example, the light polarization of the light source is not particularly controlled; however, when the efficiency for inducing LSPR on the metal particles has a light polarization dependence, it is preferable to control the light polarization.

The transmission spectrum of the whole optical element is the product of the spectra of the metal particles disposed on the both sides of the element, and hence undergoes a band narrowing effect. Additionally, in present Example, the distance between the two groups of metal microstructures is 550 µm, and the optical element is designed so that the wavelength of the light that induces the surface plasmon on the metal particles may be approximately 1100 nm in the support. Accordingly, the optical element is constructed so as for the distance between the groups of metal microstructures to be ½ of a natural number times the wavelength of the light, and hence the band narrowing of the spectrum due to a strong confinement effect is enabled.

Example 2

FIGS. 6A and 6B illustrate a sensor apparatus and a sensing method using an optical element of the present invention. The optical element includes an approximately 525-µm thick dielectric substrate 601 made of quartz, and a group 602 of metal microstructures disposed on the dielectric substrate 601. The metal microstructures 606, constituting the group 602 of metal microstructures, each are an Au thin film of approximately 20 nm in thickness.

The material for the metal particles is Au in present Example, but is not limited to Au, and is preferably a material capable of generating plasmon resonance; in particular, preferable is a metal small in dielectric loss such as Ag, Cu, Pt and Al.

The material for the dielectric substrate 601 is not limited to quartz, and is, in particular, preferably a material having a high transmittance in the wavelength region for measuring the optical spectrum.

As illustrated in FIG. 6B, the metal microstructures, constituting the group 602 of metal microstructures, each are formed as a square with a side of approximately 100 nm, and are disposed in a square lattice shape with a spacing of approximately 300 nm between the adjacent metal microstructures.

An interlayer film 604 is formed in a thickness of 1000 nm on the group 602 of metal microstructures, and a metal film 603, in place of a group of metal microstructures, is disposed on the interlayer film 604. The metal film 603 is exposed to the outside, and the group 602 of metal microstructures and the metal film 603 are separated by 980 nm from each other.

Additionally, the metal film 603 includes micro-openings 613 formed on a square lattice. The micro-openings 613 each are formed as a square with a side of approximately 100 nm, and are disposed in a square lattice shape with a spacing of 300 nm between the respective micro-openings. In present Example, the shape of the metal microstructures 606 and the shape of the micro-openings 613 were the same, but the optical element of the present invention is not limited to such same structures.

Next, the surface of the metal thin film 603 is modified with an antibody.

For example, an anti-AFP (α-fetoprotein) antibody can be immobilized as an antibody on the surface (Au) of the metal thin film 603; in this case, an ethanol solution of 11-mercaptoundecanoic acid having a thiol group is placed dropwise with a spotter or the like on the Au surface of the metal thin film 603; thus, the carboxyl groups are exposed on the surface of the metal thin film 603.

Next, in the same manner as described above, an aqueous solution of N-hydroxysulfosuccinimide and an aqueous solution of 1-ethyl-3-[3-dimethylamino]propyl carbodiimide hydrochloride are placed dropwise with a spotter or the like on the surface of the metal thin film 603, in particular, on the reaction area. Thus, the succinimide groups are exposed on the surface of the metal thin film 603.

Next, the surface of the metal thin film 603 is reacted with streptavidin, and consequently the surface is modified with streptavidin. Then, biotinylated anti-AFP antibody is immobilized on this structure. Consequently, as illustrated in FIG. 6A, the surface of the metal thin film 603 is turned into the state modified with the antibody 607, and the surface of the metal thin film 603 is turned into the surface capable of reacting with an antigen.

Figure 7:
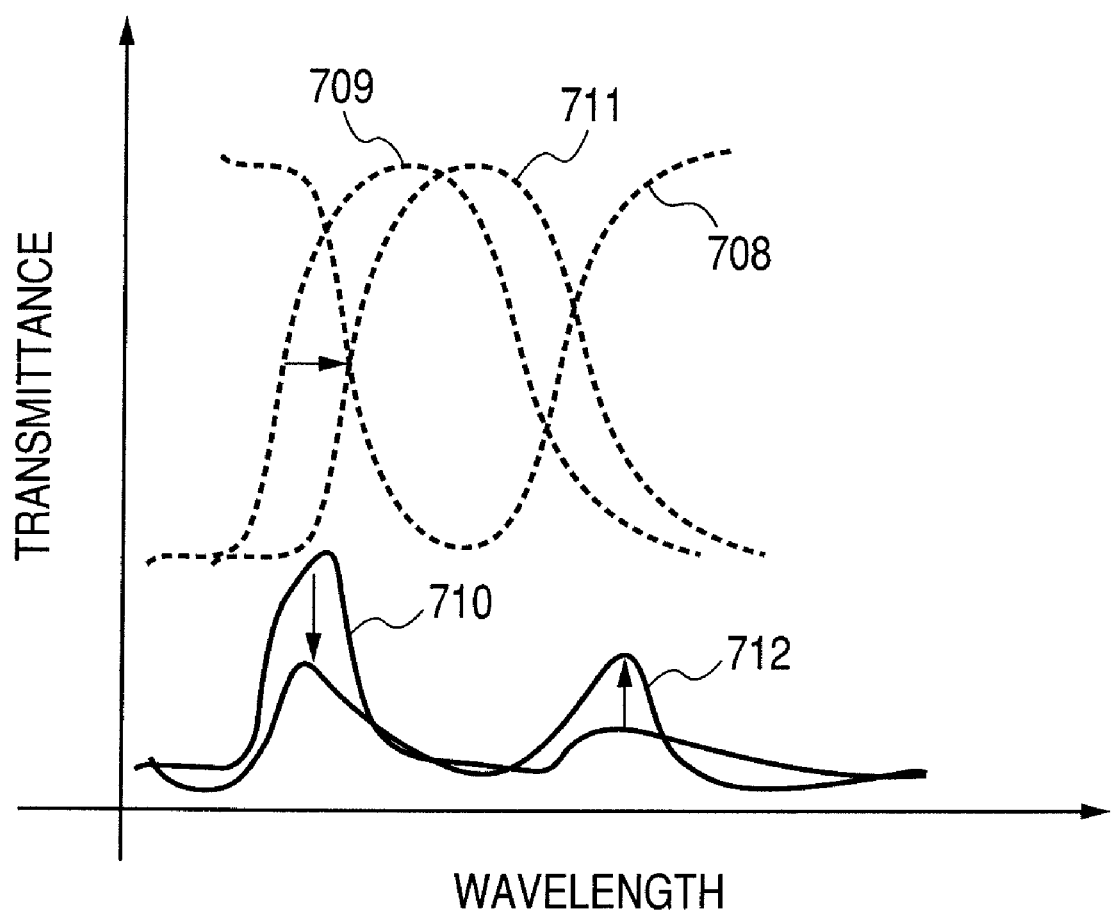
FIG. 7 shows a chart showing the measurement results of Example 2.

Next, a measurement is carried out by using the optical element thus prepared. The measurement method by using the optical element of present Example is in conformity with Example 1. The optical spectra measured with the sensor apparatus of present Example were found to be as illustrated in FIG. 7.

Specifically, the transmission spectra for the optical element before being processed with an analyte were found to be the transmission spectrum 708 of the group 602 of metal microstructures and the transmission spectrum 709 of the metal thin film 603. Additionally, the transmission spectra for the optical element after being processed with the analyte were found to be such that only the transmission spectrum of the metal thin film 603 was turned into the transmission spectrum 711. Accordingly, the transmission spectrum of the whole optical element 605 was found to be the transmission spectrum 710 before the reaction and the transmission spectrum 712 after the reaction.

As described in present Example, by carrying out the measurement by using the group of metal microstructures and the metal thin film absolutely different in transmission spectrum shape from each other, the transmission spectrum of the whole optical element were able to be largely changed in shape. Consequently, a high-sensitivity and high-precision measurement has been enabled.

In present Example, each of the metal microstructures 606 was a square thin film, but the shape of each of the metal microstructures 606 is not limited to this shape. The shape of each of the micro-openings was also a square, but is not limited to a square. The shape of the metal microstructures 606 and the shape of the micro-openings 613 each have only to be a structure capable of inducing LSPR. Additionally, in present Example, the light polarization of the light source is not particularly controlled; however, when the efficiency for inducing LSPR on the metal microstructures has a light polarization dependence, it is preferable to control the light polarization.

In present Example, an interlayer film 604 is disposed between the group of metal microstructures and the metal film. However, the member disposed between the group of metal microstructures and the metal film is not limited to the interlayer film, and a layer of air or a layer of vacuum may also be disposed. Alternatively, the involved configuration may also be such that the space between the group of metal microstructures and the metal film may also be partially filled with a dielectric or the like. The way of filling the dielectric varies the number of the metal microstructures or the micro-openings undergoing the change of the plasmon resonance conditions due to the change of the dielectric constant of the environment surrounding the optical element at the time of sensing. Accordingly, by changing the filling material in such a way as described above, the way of the change of the spectrum at the time of sensing can be varied.

Example 3

Figure 10:
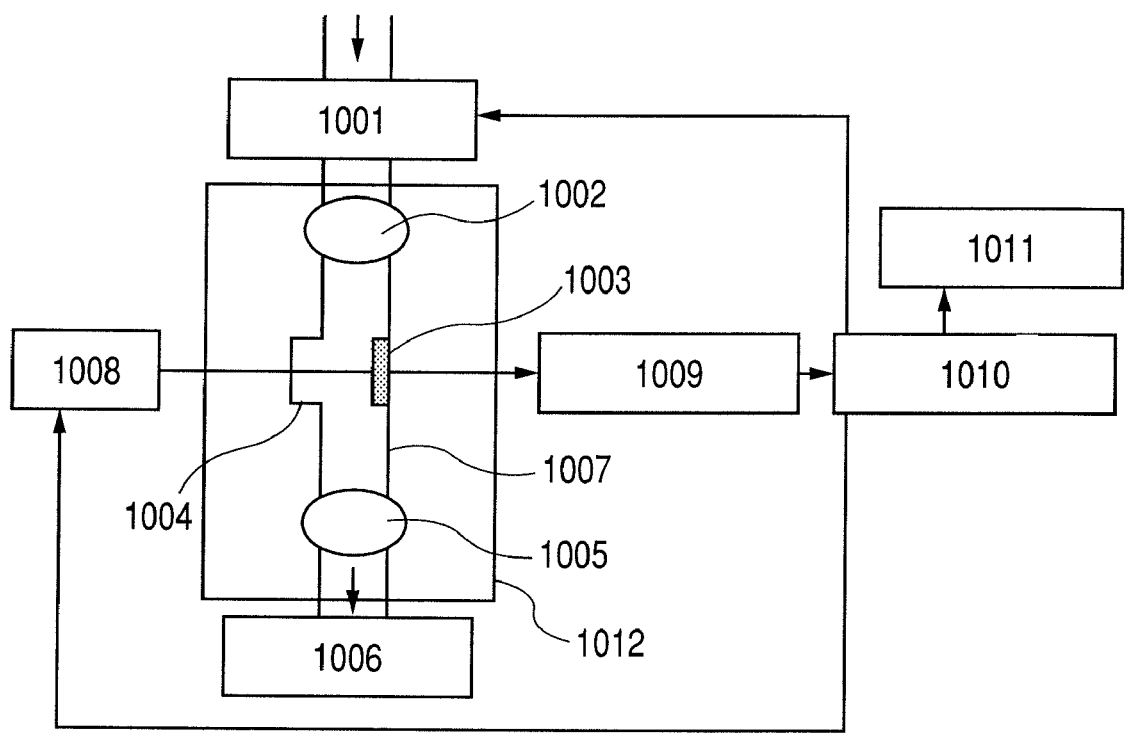
FIG. 10 shows a view illustrating the sensor apparatus of Example 3.

FIG. 10 illustrates an example of the configuration of a sensor apparatus using an optical element of the present invention. The sensor apparatus of the present invention includes a liquid transfer pump 1001, an injection opening 1002, an optical element 1003, a reaction well 1004, a discharge opening 1005 and a waste liquid reservoir 1006. The injection opening 1002, the reaction well 1004 and the discharge opening 1005 are connected by a flow path 1007. In the range from the injection opening 1002 through the reaction well 1004 to the discharge opening 1005, a reference liquid and an analyte liquid flow through the flow path 1007.

In the sensor apparatus, the light from a light source 1008 is introduced into an optical element 1003, and the transmitted light from the optical element 1003 is spectroscopically measured with a spectroscopic measurement apparatus 1009. The data thus obtained is introduced into a central processing unit 1010 to measure the optical spectrum of the transmitted light from the optical element 1003. The central processing unit 1010 displays the measurement results on a display unit 1011, and also generates the signal controlling the light source 1008.

Here, a tungsten lamp was used as the light source 1008. However, the setup of the light source is not constrained to adopt this lamp. The light source is not particularly limited as long as the light source can emit light in the measurement wavelength region.

In the present invention, by constructing the sensor apparatus as described above by using an optical element, a high-sensitivity sensing (for example, refractive index sensing and biosensing) can be carried out.

Example 4

Figure 11A:
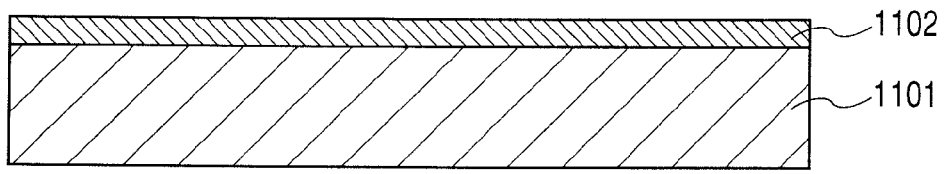
FIGS. 11A, 11B and 11C show views illustrating the optical element of Example 4.
Figure 11B:
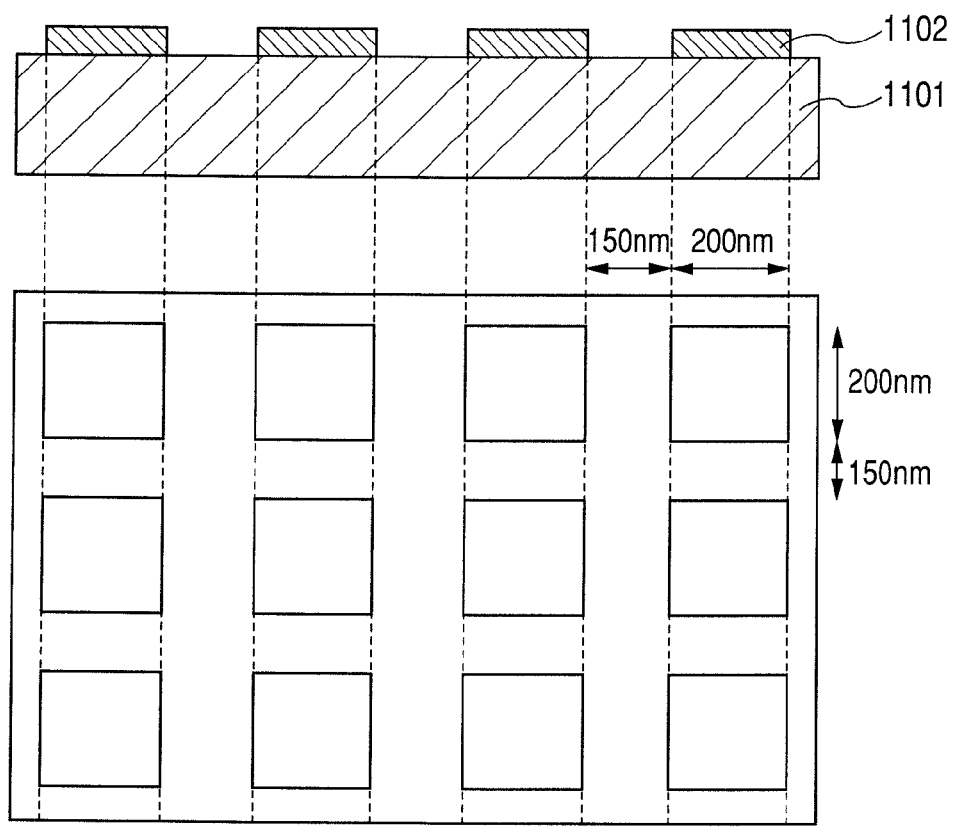
Figure 11C:
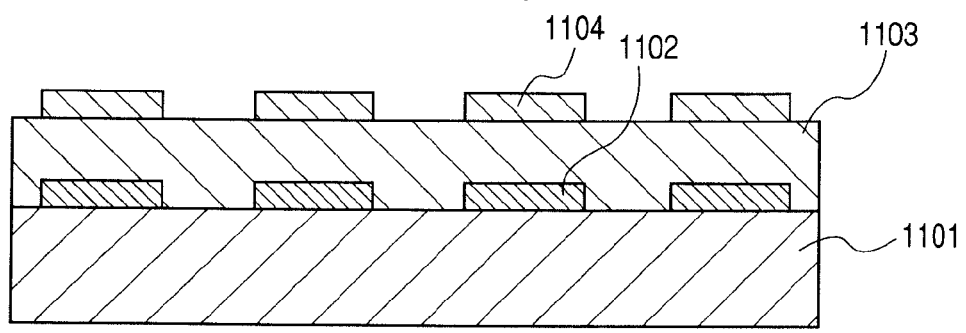

FIGS. 11A, 11B and 11C illustrate an example of the method for preparing an optical element of the present invention. First, as a dielectric substrate 1101, a 525-μm thick quartz substrate was prepared. Next, by using a sputtering apparatus, a Au film (conductive film A) was formed in a thickness of 20 nm as a metal film 1102 on the dielectric substrate 1101 (FIG. 11A). As the film forming apparatus, a CVD apparatus or a vapor deposition apparatus may be used in place of the sputtering apparatus.

Next, by using a focused ion beam (FIB) processing apparatus, the metal film 1102 was subjected to patterning. In this patterning, the patterning shape was a square with a side of 200 nm and such squares were disposed in a square lattice shape with a spacing of 150 nm. Consequently, on the dielectric substrate, a first group of metal microstructures including a plurality of metal microstructures disposed on the dielectric substrate was formed.

Here, the patterning method is not limited to the FIB method. After applying resist, a pattern is formed by using an electron beam printing apparatus or an exposure apparatus such as a stepper, and thereafter a dry etching process or a lift off process can also be used (FIG. 11B).

Next, by using a sputtering apparatus, a 500-nm thick $SiO_2$ film was formed as a dielectric layer 1103 on the pattern. Here, the film formation apparatus is not limited to a sputtering apparatus, but a CVD apparatus or a SOG apparatus may also be used.

Thereafter, by using a sputtering apparatus, an Au film (conductive film B) was formed in a thickness of 20 nm as a metal film 1104 on the dielectric layer 1103. Next, by using a focused ion beam (FIB) processing apparatus, the metal film 1104 was subjected to patterning. In this case, the pattern shape was the same as that for the metal film 1102. Consequently, the second group of metal microstructures including a plurality of metal microstructures disposed on the dielectric film was formed (FIG. 11C).

In present Example, two groups of metal microstructures were formed; however, by repeating the above-described formation of a dielectric layer and a group of metal microstructures according to need, an optical element including a desired number of dielectric layers and groups of metal microstructures can be prepared.

Figure 12:
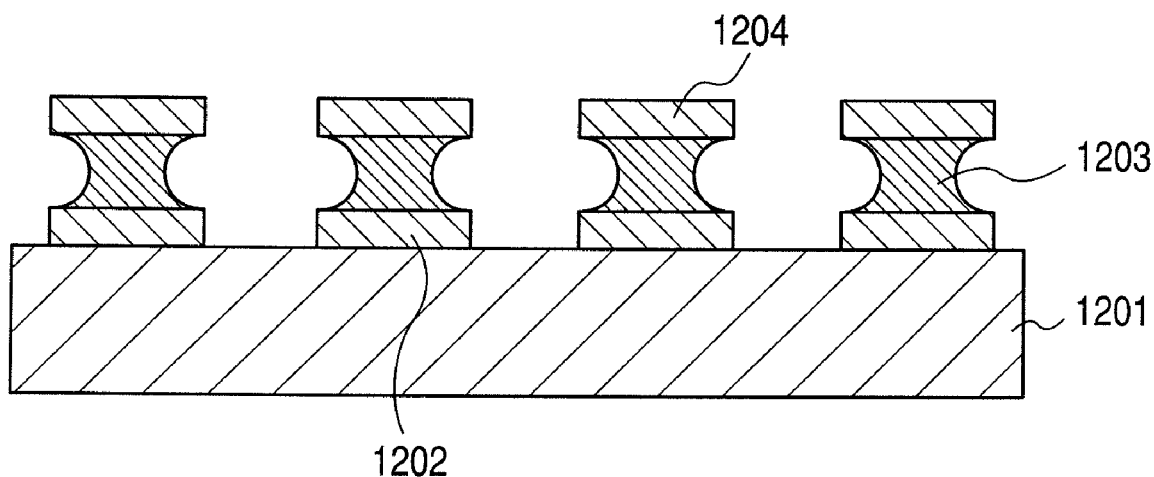
FIG. 12 shows a view illustrating the optical element of Example 4.

The space between the metal film 1102 and the metal film 1104 is not limited to the structure filled with the dielectric layer 1103 as illustrated in FIG. 11C. For example, for the optical element illustrated in FIG. 11C, the metal films 1102 and 1104 can also be processed into the shape as illustrated in FIG. 12, by subjecting the metal films 1102 and 1104 to dry etching with a mask and a fluorinated gas. In this case, by varying the etching conditions, the shape of the dielectric layer 1203 between the metal film 1202 and the metal film 1204 disposed on the substrate 1201 can be varied. For example, by setting the etching conditions so as for the isotropic etching component to be strong, the shape illustrated in FIG. 12 can be formed.

The preparation method of present Example enables the control of the optical properties of the optical element of the present invention through the shape control of the dielectric layer of the optical element.

Example 5

Figure 13A:
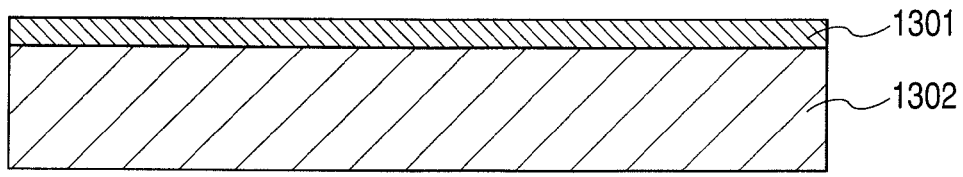
FIGS. 13A, 13B and 13C show views illustrating the optical element of Example 5.
Figure 13B:
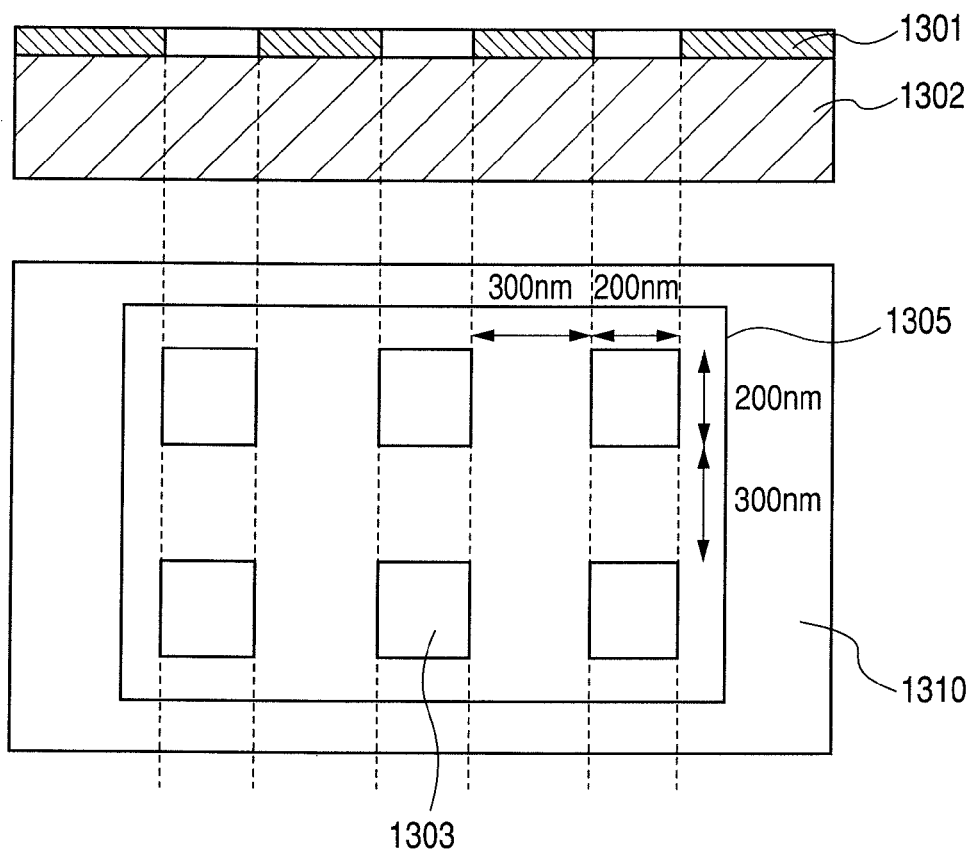
Figure 13C:
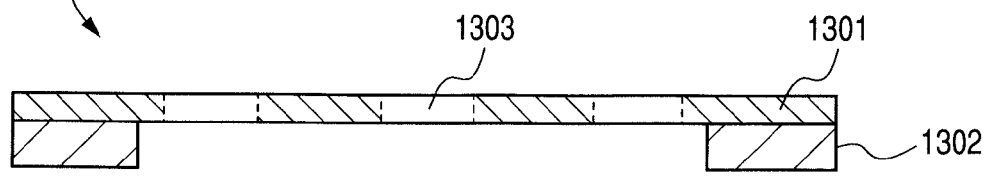

FIGS. 13A, 13B and 13C illustrate an example of another preparation method of an optical element of the present invention. In the preparation method, first, as a dielectric substrate 1302, a 525-μm thick quartz substrate was prepared (step (1)). Next, by using a sputtering apparatus, a Au film (conductive film C) was formed in a thickness of 200 nm as a metal film 1301 on the dielectric substrate 1302 (step (2)). However, the film formation apparatus is not limited to a sputtering apparatus, but a CVD apparatus or a vapor deposition apparatus may also be used.

Next, by using a focused ion beam (FIB) processing apparatus, the Au film was subjected to patterning. In this patterning, the shape of the pattern 1303 is a square opening with a side of 200 nm. Such square openings were disposed in a square lattice shape with a spacing of 300 nm between the respective openings. Consequently, a plurality of micro-openings was formed in the Au film. Thus, a group of metal microstructures was formed (step (3)).

Here, the patterning method is not limited to the FIB method. After applying resist, a pattern 1303 is formed by using an electron beam printing apparatus or a stepper, and thereafter a dry etching process or a lift off process may also be used.

Next, a resist is patterned on the backside of the dielectric substrate 1302, and thereafter the dielectric substrate was removed by dry etching so as to remain in directly beneath the periphery 1310 (the outside of the line 1305; the outside of the area surrounding the plurality of micro-openings) of the groups of metal microstructures (step (4)). Here, the etching mask is not limited to a resist, but may be a mask made of a metal or other materials.

Figure 14:
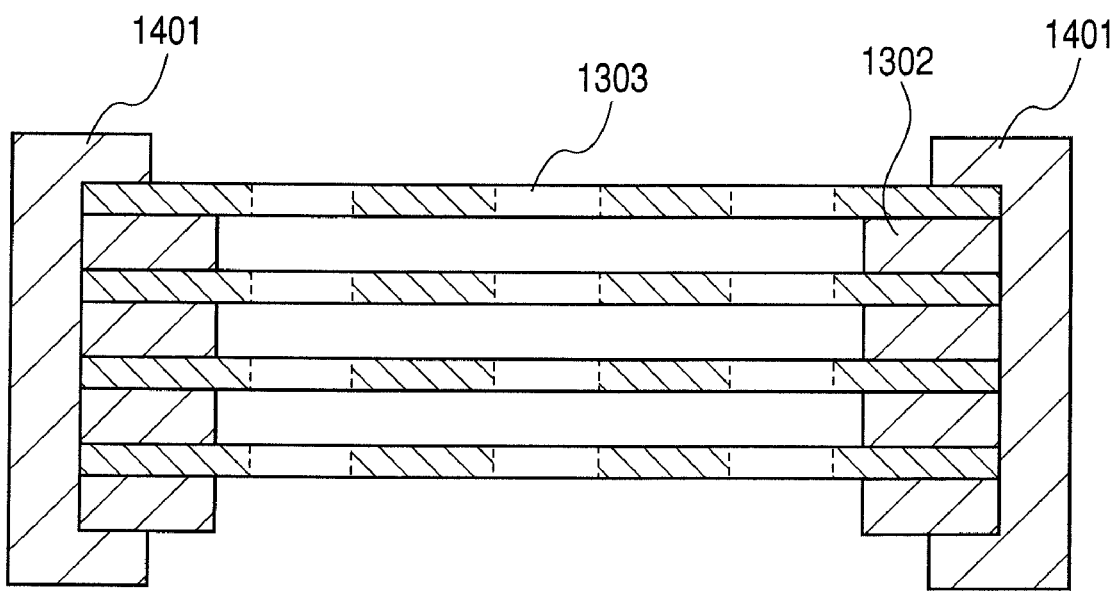
FIG. 14 shows a view illustrating the optical element of Example 5.

Additionally, by repeating the above-described steps from (1) to (4), a desired number of metal films 1304 were prepared. Next, these metal films each provided with a dielectric substrate in directly beneath the periphery were laminated and fixed. For the fixing, a fixing jig 1401 may be used as illustrated in FIG. 14, or other fixing or bonding methods may also be used.

The preparation method of present Example enables the preparation of the optical element of the present invention including self-supported metal films.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-352406, filed Dec. 27, 2006, which is hereby incorporated by reference herein in its entirety.

What is claimed is:

1. An optical element utilizing localized surface plasmon resonance, comprising:
    a dielectric substrate;
    a first group of metal microstructures in which a plurality of metal microstructures is supported on the dielectric substrate in an in-plane direction of the substrate; and
    a second group of metal microstructures in which a plurality of metal microstructures is disposed in the in-plane direction, and each of the metal microstructures is partially exposed to the outside;
    wherein the first group of metal microstructures and the second group of metal microstructures are laminated so as to be separated from each other by 100 nm or more.

2. The optical element according to claim 1, wherein the metal microstructures each comprise at least one element selected from the group consisting of gold, silver, platinum, copper and aluminum.

3. The optical element according to claim 1, wherein the metal microstructures comprised in the first group of metal microstructures or the second group of metal microstructures are disposed periodically with a specific period A.

4. The optical element according to claim 3, wherein the period A is a length of a natural number times the wavelength of the light that induces surface plasmon on the metal microstructures.

5. The optical element according to claim 1, comprising a dielectric between the first group of metal microstructures and the second group of metal microstructures.

6. The optical element according to claim 1, wherein the distance between the first group of metal microstructures and the second group of metal microstructures is a length of a natural number times the wavelength of light that induces surface plasmon on the metal microstructures.

7. The optical element according to claim 1, comprising a metal film provided with a plurality of micro-openings for the first group of metal microstructures or the second group of metal microstructures.

8. The optical element according to claim 7, wherein the metal film comprises at least one element selected from the group consisting of gold, silver, platinum, copper and aluminum.

9. The optical element according to claim 7, wherein the micro-openings are periodically disposed with a specific period B.

10. The optical element according to claim 7, wherein the period B is a length of a natural number times the wavelength of light that induces surface plasmon on the micro-openings.

11. A sensor apparatus comprising:
the optical element according to claim 7;
a light source capable of irradiating the optical element with light;
a detector capable of detecting transmitted light from the optical element; and
a vessel holding an analyte.

12. The sensor apparatus according to claim 11, wherein the light source is formed so as to be capable of irradiating light of the wavelength that induces surface plasmon on the metal microstructures or the metal film comprising the optical element.

13. A sensing method that utilizes the sensor apparatus according to claim 11, comprising the steps of:
preparing an analyte;
measuring as an optical spectrum 1 with the detector the transmitted light from the optical element obtained by irradiating the optical element with light from the light source;
processing the optical element with the analyte;
measuring as an optical spectrum 2 with the detector the transmitted light from the optical element obtained by irradiating the optical element which has been subjected to the processing, with light from the light source; and
detecting the analyte by measuring the change between the optical spectrum 1 and the optical spectrum 2.

14. The sensing method according to claim 13, wherein the analyte is a biological molecule.

15. The sensing method according to claim 13, wherein in the detecting step, the concentration of the analyte is detected by measuring the magnitude of the change between the optical spectrum 1 and the optical spectrum 2.

16. A sensor apparatus comprising:
the optical element according to claim 1;
a light source capable of irradiating the optical element with light;
a detector capable of detecting transmitted light from the optical element; and
a vessel holding an analyte.

17. The sensor apparatus according to claim 16, wherein the light source is formed so as to be capable of irradiating light of the wavelength that induces surface plasmon on the metal microstructures or the metal film comprising the optical element.

18. A sensing method that utilizes the sensor apparatus according to claim 16, comprising the steps of:
preparing an analyte;
measuring as an optical spectrum 1 with the detector the transmitted light from the optical element obtained by irradiating the optical element with light from the light source;
processing the optical element with the analyte;
measuring as an optical spectrum 2 with the detector the transmitted light from the optical element obtained by irradiating the optical element which has been subjected to the processing with light from the light source; and
detecting the analyte by measuring the change between the optical spectrum 1 and the optical spectrum 2.

19. The sensing method according to claim 18, wherein the analyte is a biological molecule.

20. The sensing method according to claim 18, wherein in the detecting step, the concentration of the analyte is detected by measuring the magnitude of the change between the optical spectrum 1 and the optical spectrum 2.

* * * * *